United States Patent [19]

D'Amico

[11] 4,432,785
[45] Feb. 21, 1984

[54] N-SUBSTITUTED-OXOBENZOTHIAZOLINE DERIVATIVES USEFUL AS PLANT GROWTH REGULANTS

[75] Inventor: John J. D'Amico, Creve Coeur, Mo.

[73] Assignee: Monsanto Company, St. Louis, Mo.

[21] Appl. No.: 325,468

[22] Filed: Nov. 27, 1981

[51] Int. Cl.³ ............................................. A01N 43/78
[52] U.S. Cl. ............................................ 71/90; 71/76
[58] Field of Search ........................................ 71/90, 76

[56] References Cited

U.S. PATENT DOCUMENTS

| | | | |
|---|---|---|---|
| 3,069,429 | 12/1962 | Godson et al. | 71/90 |
| 3,651,074 | 3/1972 | D'Amico | 71/90 |
| 3,839,349 | 10/1974 | Wagner et al. | 71/90 |
| 4,049,419 | 2/1976 | D'Amico | 71/76 |
| 4,160,658 | 7/1979 | D'Amico | 71/90 |

*Primary Examiner*—Catherine L. Mills
*Attorney, Agent, or Firm*—Richard H. Shear; Patricia A. Coburn; J. Timothy Keane

[57] ABSTRACT

The present invention relates to the use of compounds of the formula

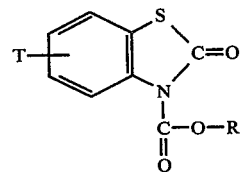

wherein R is $C_{1-5}$ alkyl, $C_{2-5}$ alkenyl, $C_{2-5}$ alkynyl, haloalkyl, phenyl or phenyl substituted by one or two halogen, $C_{1-5}$ alkyl, $C_{1-5}$ alkoxy or haloalkyl moieties; T is equal to $C_{1-5}$ alkyl, $C_{1-5}$ alkoxy, halogen, or haloalkyl in a method of regulating plant growth, especially leguminous plant growth, as well as to plant growth regulant compositions.

9 Claims, No Drawings

N-SUBSTITUTED-OXOBENZOTHIAZOLINE DERIVATIVES USEFUL AS PLANT GROWTH REGULANTS

BACKGROUND OF THE INVENTION

This invention relates to certain N-substituted oxobenzothiazolines which are useful in a method of regulating plant growth, especially leguminous plant growth, as well as to plant growth regulant compositions. Compounds which are useful in regulating the growth and development of crop plants have become increasingly important as the rapidly increasing world population continues to greatly increase the pressure on available world food supplies. An increase in food production through increased land utilization is not a viable solution to this problem because, although more land can be put into production than is now being cultivated, much of that land is marginal and may, in order to be productive, require substantial inputs of water and fossil fuel energy, which are themselves diminishing resources. As a result, the use of chemicals to produce yield increases through the physiological manipulation of the crop plant offers an important means of increasing crop yield.

SUMMARY OF THE INVENTION

This invention is concerned with N-substituted 2-oxo-3-benzothiazoline derivatives which are useful in regulating the growth of plants, especially leguminous plants. The invention further relates to the use of the 2-oxo-3-benzothiazoline derivatives described herein in plant growth regulant compositions.

DESCRIPTION OF THE INVENTION

The compounds of the present invention which have been found to be effective in the regulation of plant growth, especially leguminous plant growth, are N-substituted-2-oxo-3-benzothiazoline derivatives of the formula

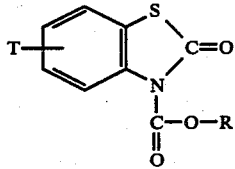

wherein R is equal to $C_{1-5}$ alkyl, $C_{2-5}$ alkenyl, $C_{2-5}$ alkynyl, haloalkyl, phenyl or phenyl substituted by one or two halogen, $C_{1-5}$ alkyl, $C_{1-5}$ alkoxy or haloalkyl moieties; T is equal to $C_{1-5}$ alkyl, $C_{1-5}$ alkoxy, halogen or haloalkyl.

In the description of the N-substituted oxobenzothiazoline derivatives useful as plant growth regulants according to this invention, the following embodiments are intended for the various groups. The term "$C_{1-5}$ alkyl" includes those members including straight chain and branched chain, having from 1 to 5 carbon atoms, inclusive, for example, methyl, ethyl, n-propyl, isopropyl, n-butyl, sec-butyl, tert-butyl, n-pentyl, isopentyl, and the like.

The term "$C_{2-5}$ alkenyl" are those straight or branched chain radicals, having from 2 to 5 carbon atoms and preferably from 3 to 5 carbon atoms and exemplified by 2-propenyl, 1-methyl-2-propenyl, 2-methyl-2-propenyl, 2-butenyl, 1-methyl-2-butenyl, 2-methyl-2-butenyl, 3-butenyl, 1-methyl-3-butenyl or 2-methyl-3-butenyl and the like. The term "$C_{2-5}$ alkynyl" are those straight or branched chain radicals, having from 2 to 5 carbon atoms and exemplified by ethyne, propyne, 1-butyne, 1-pentyne, 2-butyne, 2-pentyne and the like.

The term "haloalkyl" as employed herein designates an alkyl moiety having up to 5 carbon atoms wherein at least one hydrogen atom has been replaced by a halogen group. Illustrative groups are chloromethyl, iodobutyl, dichloroethyl, dibromopropyl, trichloromethyl, trifluoromethyl and the like. Where the term "halo" or "halogen" is used herein, it is understood to mean chlorine, bromine, fluorine and iodine. The term "$C_{1-5}$ alkoxy" preferably includes those members, including straight chain and branched chain, having from 1 to 5 carbon atoms, inclusive, for example, methoxy, ethoxy, n-propoxy, isopropoxy, n-butoxy, sec-butoxy, tert-butoxy, n-butoxy, isopentoxy and the like.

The term "active ingredient" is used herein to describe the N-substituted-2-oxo-3-benzothiazoline derivatives of the formula previously described. The N-substituted oxobenzothiazoline compounds found to be useful in regulating the growth of leguminous plants may be prepared according to the general procedure described in Example 1.

EXAMPLE 1

To a stirred charge maintained at 0° C. containing 0.1 mole of the appropriate 2-hydroxybenzothiazole, 300 ml of acetone, 11.4 gram (0.11 mole) of triethylamine and 20 ml of water, was added dropwise, 0.1 mole of the appropriate substituted chloroformate at 0°–10° C. The reaction mixture was stirred at 25°–30° C. for 24 hours. After cooling the mixture to 5° C., 800 grams of ice water was added and stirring continued at 0°–10° C. for 30 minutes. The solid was collected by filtration, washed with water until neutral to litmus and air-dried at 25°–30° C. The procedure was followed for all compounds described in Table I except for the compound of Example No. 5 which was cooled to 25° C. and thereafter 400 ml of water and 500 ml of ethyl ether were added to the reaction mixture and stirring was continued for 15 minutes. The separated ether layer was then washed with water until neutral to litmus and dried over sodium sulfate. The ether was removed in vacuo at the maximum temperature of 80°–90° C. at 1–2 mm Hg.

The data obtained when the N-substituted-2-oxo-3-benzothiazoline compounds described herein were prepared in accordance with Example 1 are described in Table I below.

TABLE I

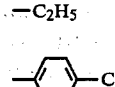

| Example No. | T | R | % Yield | M.P. °C. | % C Calc'd | % C Found | % H Calc'd | % H Found | % N Calc'd | % N Found | % S Calc'd | % S Found |
|---|---|---|---|---|---|---|---|---|---|---|---|---|
| 1 | H | —$CH_3$ | 93 | 47–7[a] | 51.67 | 51.65 | 3.37 | 3.37 | 6.70 | 6.67 | 15.33 | 15.31 |
| 2 | H | —$C_2H_5$ | 96 | 67–8 | 53.80 | 53.91 | 4.06 | 4.10 | 6.27 | 6.24 | 14.36 | 14.33 |
| 3 | H | —$CH(CH_3)_2$ | 67 | 74–5[a] | 55.68 | 55.50 | 4.67 | 4.71 | 5.90 | 5.85 | 13.51 | 13.60 |
| 4 | H | —$C_3H_7$ | 98 | 64–5[a] | 55.68 | 55.73 | 4.67 | 4.69 | 5.90 | 5.88 | 13.51 | 13.51 |
| 5 | H | —$C_4H_9$ | 92 | liquid $N_D^{25} = 1.5631$ | 57.35 | 57.12 | 5.21 | 5.24 | 5.57 | 5.51 | 12.76 | 12.69 |
| 6 | H | —$CH_2CH=CH_2$ | 85 | 78–9[a] | — | — | — | — | 5.95 | 5.78 | 13.63 | 13.67 |
| 7 | H | —$C_6H_5$ | 99 | 92–3[a] | 61.98 | 61.90 | 3.84 | 3.37 | 5.16 | 5.15 | 11.82 | 11.79 |
| 8 | H | —$CH_2CH(CH_3)_2$ | 97 | 33–4 | 57.35 | 57.16 | 5.21 | 5.25 | 5.57 | 5.54 | 12.76 | 12.75 |
| 9 | 6-Br | —$CH_3$ | 83 | 167–8 | 37.52 | 37.58 | 2.10 | 2.13 | 4.86 | 4.85 | 11.13 | 11.13 |
| 10 | 6-$OC_2H_5$ | —$CH_3$ | 93 | 151–2[b] | 52.16 | 52.27 | 4.38 | 4.43 | 5.53 | 5.52 | 12.66 | 12.72 |
| 11 | 6-Br | —$C_2H_5$ | 93 | 75–6[b] | 39.75 | 39.76 | 2.67 | 2.70 | 4.64 | 4.65 | 10.61 | 10.58 |
| 12 | 6-$OC_2H_5$ | —$C_2H_5$ | 97 | 89–91[b] | 53.92 | 53.99 | 4.90 | 4.93 | 5.24 | 5.22 | 12.00 | 11.97 |
| 13 | H | 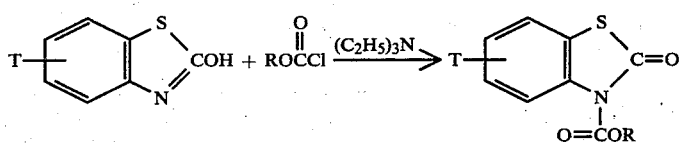 | 77 | 82–4 | 49.43 | 49.80 | 2.07 | 2.52 | 4.12 | 4.49 | 9.43 | 9.15 |

[a] Recrystallization from heptane/isopropyl alcohol.
[b] Recrystallization from isopropyl alcohol.

Compounds of the formula described above have been found to produce a variety of plant growth regulatory responses when applied to crop plants, especially leguminous crop plants, as for example, soybean (Glycine max). The terms "plant growth regulant effect", "plant growth regulation" or words to that effect are used in this specification and in the claims to mean the causation by the chemicals of the present invention, of a variety of plant responses which achieve a desirable promotion, inhibition or modification of any plant physiological or morphological process. It should additionally be recognized that various plant responses may also result from a combination or sequence of both physiological and morphological factors.

The plant growth regulant effects which may be produced in crop plants, especially leguminous crop plants, using the method of the present invention are probably most readily observable as changes in the size, shape, color or texture of the treated plant or any of its parts. Similarly, changes in the quantity of the plant fruit or flowers are also quite apparent from visual inspection. The above changes may be characterized as an acceleration or retardation of plant growth, stature reduction, leaf or canopy alteration, increased branching, tillering, terminal inhibition, increased flowering or fruit set, increased root growth, axillary bud development or inhibition, delayed budding, increased cold hardiness, delayed or accelerated ripening, and the like.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatues and are more resistant to pest infestations and to lodging. Reduction in the maturation rate on portions of a crop permits an extended harvest period at peak yield and more efficient use of subsequent crop processing equipment. Suppression of vegetative growth at the appropriate stage of the plant's development may result in increased energy available for utilization in reproductive development so that, for example, more fruit or larger fruit is formed.

Increased plant dry matter accumulation is a valuable plant growth regulant response which can occur in conjunction with morphological changes or can be the sole plant growth response detected. Increased dry matter accumulation is the physically measurable manifestation of increased plant photosynthetic activity. Most plants capture no more than 1 to 3 percent of the solar energy they receive. Present knowledge suggests that it is theoretically possible to increase this rate to approximately twelve percent. Enhancement of photosynthesis at the appropriate stage of the plant's growth and development may enable the plant to fix more carbon dioxide resulting in the production of increased amounts of carbohydrate, amino acids, etc., which could be available for utilization in the plant's reproductive activities, leading to increased crop yields.

It is to be understood that the regulation of desirable crop plants in accordance with the instant invention does not include the total inhibition or the killing of such plants. It is contemplated herein to employ only plant regulating amounts of the compounds described above in order to modify the normal sequential development of the treated plant to agricultural maturity. The application of a plant regulating amount may be applied to plants in sequence at various stages of the plant's development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention it has been found that desirable modification of crop plants, preferably leguminous crop plants, is achieved by applying the above-described plant growth regulants to the "plant" or plant "habitat". The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulatiing compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The compositions can also be applied from airplanes as a dust or spray. Should the application of the plant growth composition to the plant growth medium be desired, this is accomplished by incorporating the compositions in the soil or other media in the area where modifications of the plants is desired.

Compositions of this invention generally contain from about 5 to 95 parts active ingredient, about 1 to 50 parts surface-active agent, dispersant or the like, and about 5 to 94 parts solvent or carrier, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from 0.50 to about 5 pounds per acre. Preferred are foliar applications of from 0.50 to 5 pounds of the active ingredient per acre. In application to the soil habitat of germinant seeds, emerging seedlings and established vegetation for the regulation of plant growth, the active ingredients are applied in amounts of from 0.1 to about 5 pounds per acre or more. The application to the soil of from 0.1 to about 3 pounds of active ingredient per acre is preferred. Foliar application to plants beginning to blossom are preferred over other types of applications.

In accordance with the practice of the invention, several plant growth regulating compositions were formulated by mixing various N-substituted 2-oxo-3-benzothiazoline compounds as the active ingredient with acetone containing a surfactant and tested in accordance with the procedure described in Example 2.

EXAMPLE 2

A number of soybean plants, variety Williams, were grown from seeds in plastic pots in the greenhouse for a period of one week at which time the plants were thinned to one plant per pot. When the second trifoliate leaf (three weeks) was fully expanded, the plants were treated with a solution of the active ingredient in acetone and water. Aqueous TWEEN 20 was used as a surfactant.

When the fifth trifoliate leaf (four to five weeks) was fully expanded, the treated plants were compared with the non-treated control plants and the observations recorded.

Table II below summarizes the results and observations made in accordance with the above procedure.

TABLE II

| Compound of Example No. | Lbs Acre | Kilos Hectare | % Dry* Weight | Response |
|---|---|---|---|---|
| 13 | 0.1 | 0.14 | 90 | No response noted. |
|  | 0.5 | 0.56 | 83 | No response noted. |
|  | 2.5 | 2.80 | 76 | Leaf distortion, leaf alteration, leaf alteration new growth, slight leaf burn. |
| 10 | 0.1 | 0.14 | 103 | No response noted. |
|  | 0.5 | 0.56 | 79 | No response noted. |
|  | 2.5 | 2.80 | 86 | Leaf alteration, slight leaf burn. |
| 11 | 0.1 | 0.14 | 119 | No response noted. |
|  | 0.5 | 0.56 | 90 | No response noted. |
|  | 2.5 | 2.80 | 82 | Leaf distortion, altered canopy, leaf inhibition, leaf alteration new growth, moderate leaf burn. |
| 11 | 0.1 | 0.14 | 111 | No response noted. |
|  | 0.5 | 0.56 | 92 | No response noted. |
|  | 2.5 | 2.80 | 61 | Leaf alteration, leaf inhibition, leaf distortion, leaf alteration new growth, slight leaf burn. |
| 12 | 0.1 | 0.14 | 108 | No response noted. |
|  | 0.5 | 0.56 | 89 | Slight leaf burn, leaf alteration. |

TABLE II-continued

| Compound of Example No. | Lbs/Acre | Kilos/Hectare | % Dry* Weight | Response |
|---|---|---|---|---|
|  | 2.5 | 2.80 | 56 | Stature reduction, leaf distortion, leaf alteration, leaf inhibition, leaf alteration new growth, slight leaf burn. |
| 8 | 0.1 | 0.14 | 84 | No response noted. |
|  | 0.5 | 0.56 | 76 | No response noted. |
|  | 2.5 | 2.80 | 69 | Stature reduction, leaf distortion, leaf inhibition, leaf alteration, leaf alteration new growth, slight leaf burn. |
| 5 | 0.1 | 0.14 | 75 | No response noted. |
|  | 0.5 | 0.56 | 75 | Leaf alteration. |
|  | 2.5 | 2.80 | 60 | Leaf distortion, leaf inhibition, leaf alteration, leaf alteration new growth, slight leaf burn. |
| 4 | 0.1 | 0.14 | 87 | No response noted. |
|  | 0.5 | 0.56 | 90 | No response noted. |
|  | 2.5 | 2.80 | 74 | Leaf alteration new growth, leaf alteration, leaf distortion, leaf inhibition, slight leaf burn. |
| 6 | 0.1 | 0.14 | 106 | No response noted. |
|  | 0.5 | 0.56 | 82 | Slight leaf burn. |
|  | 2.5 | 2.80 | 48 | Stature reduction, altered canopy, selected apical kill, leaf distortion, severe leaf burn. |
| 7 | 0.1 | 0.14 | 92 | No response noted. |
|  | 0.5 | 0.56 | 79 | No response noted. |
|  | 2.5 | 2.80 | 35 | Leaf alteration new growth, leaf distortion, leaf inhibition, altered canopy, moderate leaf burn. |
| 3 | 0.1 | 0.14 | 90 | No response noted. |
|  | 0.5 | 0.56 | 80 | No response noted. |
|  | 2.5 | 2.80 | 53 | Leaf alteration, leaf distortion, slight leaf burn, leaf alteration new growth, leaf inhibition. |
| 2 | 0.1 | 0.14 | 102 | No response noted. |
|  | 0.5 | 0.56 | 83 | No response noted. |
|  | 2.5 | 2.80 | 68 | Leaf alteration, leaf distortion, slight leaf burn, leaf inhibition, leaf alteration new growth. |
| 1 | 0.1 | 0.14 | 97 | No response noted. |
|  | 0.5 | 0.56 | 99 | Slight leaf burn. |
|  | 2.5 | 2.80 | 65 | Leaf distortion, altered canopy, moderate leaf burn. |

*Calculated as percent control

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

I claim:

1. A method of regulating the natural growth and development of crop plants which comprises applying to the plant locus an effective plant regulating, non-lethal, amount of a compound of the formula

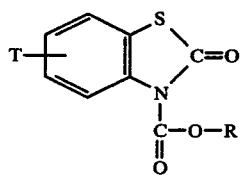

wherein R is equal to $C_{1-5}$ alkyl, $C_{2-5}$ alkenyl, $C_{2-5}$ alkynyl, haloalkyl, phenyl or phenyl substituted by one or two halogen, $C_{1-5}$ alkyl, $C_{1-5}$ alkoxy or haloalkyl moieties; T is equal to $C_{1-5}$ alkyl, $C_{1-5}$ alkoxy, halogen or haloalkyl.

2. A method according to claim 1 wherein R is $C_{1-5}$ alkyl or phenyl.

3. A method according to claim 1 wherein R is $C_{2-5}$ alkenyl, $C_{2-5}$ alkynyl or haloalkyl.

4. A method according to claim 2 wherein R is $C_{1-5}$ alkyl.

5. A method according to claim 4 wherein T is halogen.

6. A method according to claim 4 wherein R is methyl or ethyl.

7. A method according to claim 1 wherein said compound is

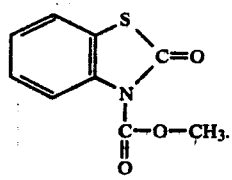

8. A method according to claim 1 wherein said compound is

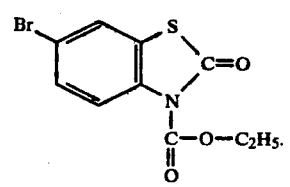

9. A method according to claim 1 wherein said crop plant is a leguminous crop plant.

* * * * *